United States Patent
Charvin et al.

(10) Patent No.: US 6,944,502 B2
(45) Date of Patent: Sep. 13, 2005

(54) METHOD AND APPARATUS FOR PICKING UP AUDITORY EVOKED POTENTIALS

(76) Inventors: Guy Charvin, 25 Chemin de la Peyrigone, 06600 Antibes (FR); Thomas Lenarz, Aussiger Wende 7b, 50559 Hannover (DE); Rolf-Dietter Battmer, Kelbshof 4, 50539 Hannover (DE)

( * ) Notice: Subject to any disclaimer, the term of this patent is extended or adjusted under 35 U.S.C. 154(b) by 446 days.

(21) Appl. No.: 10/055,090

(22) Filed: Jan. 22, 2002

(65) Prior Publication Data

US 2002/0095194 A1 Jul. 18, 2002

Related U.S. Application Data

(63) Continuation-in-part of application No. 09/496,691, filed on Feb. 2, 2000, now Pat. No. 6,428,484.

(30) Foreign Application Priority Data

| Jan. 5, 2000 | (FR) | ............................................. 00 00089 |
| Jan. 27, 2000 | (FR) | ............................................. 00 01126 |

(51) Int. Cl.$^7$ ............................................................ A61N 1/05
(52) U.S. Cl. ............................................ 607/57; 600/559
(58) Field of Search ............................. 607/55, 56, 57; 600/559, 373

(56) References Cited

U.S. PATENT DOCUMENTS

| 5,660,184 | A |   | 8/1997 | Donehoo et al. ............ 128/696 |
| 5,755,747 | A |   | 5/1998 | Daly et al. ..................... 607/55 |
| 5,758,651 | A |   | 6/1998 | Nygard et al. ............... 128/741 |
| 5,899,847 | A | * | 5/1999 | Adams et al. ................. 600/25 |
| 6,415,185 | B1 | * | 7/2002 | Maltan ......................... 607/57 |

FOREIGN PATENT DOCUMENTS

| WO | WO 97/09863 | 3/1997 | ........... H04R/25/00 |
| WO | WO97/32629 | 9/1997 | ............ A61N/1/32 |
| WO | WO 97/48447 | 12/1997 | ............ A61N/1/36 |

OTHER PUBLICATIONS

*Potentiels Evoques Auditifs* ("Auditory evoked potentials"), by J.M. G'uerit, 1993, published by Masson, PARIS, pp. 87–89.

*Electrically evoked whole-nerve action potentials: Data from human coachlear implant users*, by Carolyn J. Brown et al., published in J. Acous T Soc AM, vol. 88, No. 3, Sep. 1990, pp. 1385–1391.

French Search Report dated Oct. 2000 (in French, with copies of cited art above).

Ear & Hearing, Apr. 2000, "*The Relationship Between EAP and EABR Thresholds and Levels Used to Program the Nucleus 24 Speech Processor: Data from Adults*", Carolyn J. Brown et al., pp. 151–163.

Ear & Hearing, Apr. 2000, "*Comparison of EAP Thresholds with MAP Levels in the Nucleus 24 Cochlear Implant: Data from Children*", Michelle L. Hughes et al., pp. 164–175.

* cited by examiner

*Primary Examiner*—Scott M. Getzow
(74) *Attorney, Agent, or Firm*—Cohen, Pontani, Lieberman & Pavane

(57) ABSTRACT

The present invention relates to a device for picking up biological electrical signals, and more precisely auditory evoked potentials generated by acoustic and/or electrical and/or mechanical stimulation of the cochlea, or of a portion of the auditory system in man or animal. The device for measuring or picking up auditory evoked potentials is surgically implantable in the temporo-occipital area and comprises at least two extracochlear pickup electrodes connected to the inputs of a differential amplifier.

15 Claims, 5 Drawing Sheets

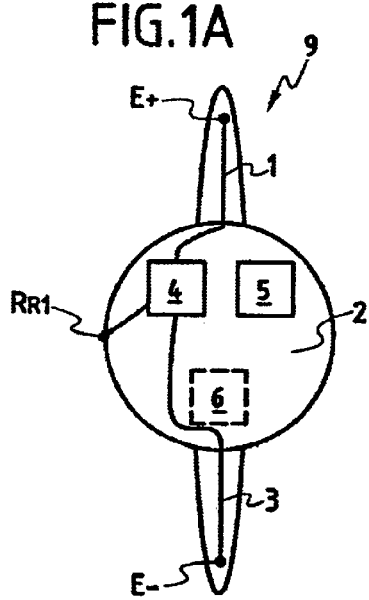
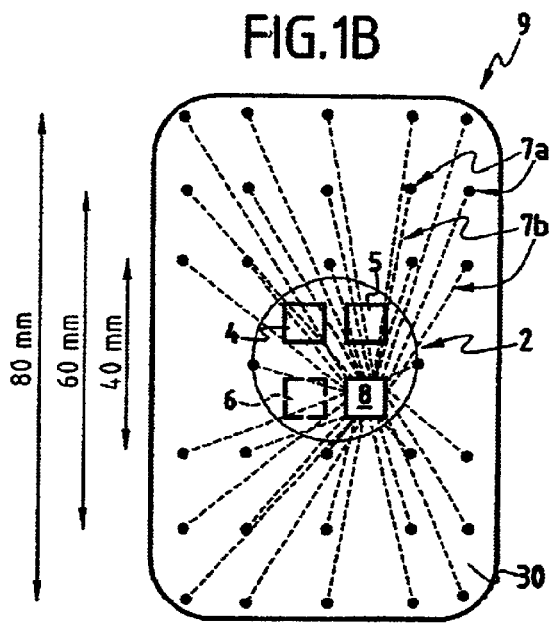
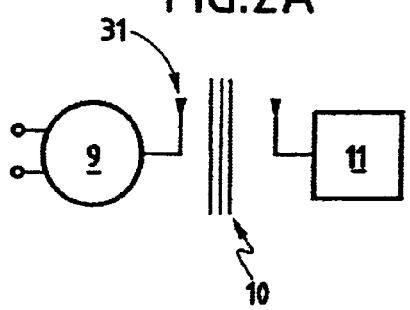
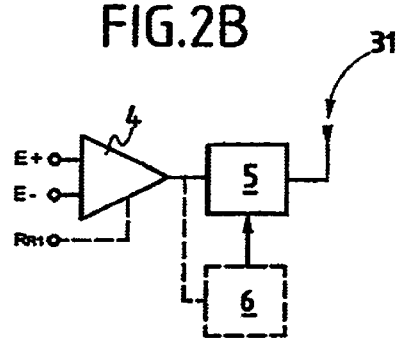
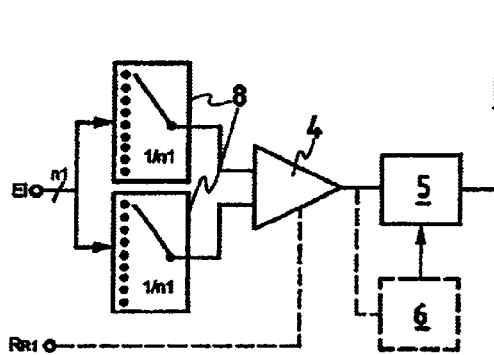

METHOD AND APPARATUS FOR PICKING UP AUDITORY EVOKED POTENTIALS

CROSS REFERENCE TO RELATED APPLICATIONS

This application is a Continuation-in-Part of U.S. patent application Ser. No. 09/496,691, filed Feb. 2, 2000 now U.S Pat No. 6,428,484, which claims priority from Applications filed in France on Jan. 05, 2000, No. 00 00089, France on Jan. 27, 2000, No. 00 01126, respectively. The disclosure of U.S. patent application Ser. No. 09/496,691 is incorporated herein by reference.

FIELD OF THE INVENTION

The present invention relates to apparatus for picking up electrical biological signals, and more specifically auditory evoked potentials generated by acoustic and/or electrical and/or mechanical stimulation of the cochlea, or of a portion of the auditory system in man or animal.

BACKGROUND OF THE INVENTION

Traditionally, auditory evoked potentials are measured with extracorporeal devices using surface electrodes applied to the skin of the patient. Such equipment picks up far field auditory evoked potentials which mainly comprise:

- early auditory evoked potentials (commonly referred to by the initials ABR). These potentials are normally made up of seven waves ("Les potentiels évoqués auditifs" [Auditory evoked potentials] by J. M. Guerit, 1993 published by Masson, Paris at pages 87 to 99 on evoked potentials), with the wave 1 being generated mainly by ramifications of the auditory nerve along the internal hair cells;
- medium latency auditory evoked potentials (referred to by initials AMLR);
- late auditory evoked potentials (referred to by the initials ALCR) and;
- cognitive evoked potentials (referred to by the initials ACR).

Such extracorporeal devices for picking up auditory potentials require a great deal of care and time to be put into operation. In addition, on safety grounds, it is essential to have complete metallic isolation between the machine and the person under test. The results obtained do not always accurately represent real auditory activity since standard equipment is specifically too sensitive to interfering electrical noise: stimulation artifacts; 50 Hz or 60 Hz from the electricity mains; high frequency interference; etc . . . Similarly, such equipment is distributed by non-auditory biological activity. Furthermore, result reproducibility is degraded by fluctuations in the resistivity of the skin and by impedance drift due in particular to moving electrodes which can shift during a test, and which above all can be positioned differently from one examination to another. In order to restrict these drawback at least in part, it is possible to make use of anesthetics, in particular when performing tests on children, but that can give rise to other non-negligible drawbacks.

There also exist implanted devices for picking up auditory evoked potentials such as those described in patent U.S. Pat. No. 5,758,651 or application WO 97/48447, which measure cochlear activity following electrical stimulation thereof.

Document U.S. Pat. No. 5,758,651 describes a telemetry system for a hearing prosthesis, in particular for a cochlear implant. The system has a plurality of electrodes which are used to stimulate the auditory nerve and to detect the evoked potentials; in an example described in that document, the potential difference between an intracochlear electrode and an extracochlear electrode is measured; that potential difference is applied to the input of a "blanking" amplifier of gain adjustable over the range 40 dB to 80 dB; in variant, that document proposes using a differential amplifier.

Document WO 97/48447 describes an adjustment system integrates in a cochlear stimulation implant; the system uses two means for measuring auditory perception by the patient: firstly an intracochlear electrode for measuring auditory perception by the patient: firstly an intracochlear electrode for measuring evoked potential, and secondly an electrode (or transducer) for measuring the activity of one of the two muscles of the middle ear ("stapedius" and "tensor tympani").

The document by Caroline J. Brown et al. Published in J. Acous T Soc AM, Vol. 88, No. 3, September 1990, pages 1385 1391, describes a method of measuring evoked potentials in which use is made firstly of one of six intracochlear electrodes of the stimulation implant, an d secondly of an electrode placed on the temporal muscle.

Those devices pick up solely a near field auditory evoked potential because one of the pickup electrodes is immersed in the cochlea and is as close as possible to the activity to be measured. That near field potential which represents the initial excitation of the auditory system is commonly referred to as evoked action potential (EAP). It does not give information about the other levels of the auditory system: cochlear nucleus, coliculus inferior, primary and secondary auditory areas, associative areas. Furthermore, EAP cannot be recorded directly because of artifacts generated by electrical stimulation too close the pickup electrodes. In order to obtain a meaningful EAP, it is necessary to make use of so-called "subtractive" techniques that serve to remove the artifacts and allow the EAP to be extracted on its own. Both techniques are described ion particular in the above-mentioned document By Carolyn J. Brown et al.

OBJECTS AND SUMMARY OF THE INVENTION

The device of the invention makes it possible to remedy the drawbacks of existing evoked potential pickup devices.

In a first aspect, the invention consists in such a device which includes at least two extracochlear pickup electrodes designed to be implanted under the skin in the temporo-occipital area of the patient, which pickup electrodes are connected to input terminals of an amplifier module integrated in a package, likewise designed to be implanted; in addition, the package includes a system for transmission through the skin, with or without signal processing, thereby enabling an external device to receive information concerning the auditory evoked potentials that have been picked up. Such a device enables activity to be recorded at each level of the auditory system and to evaluate periodically the functional state of the auditory as a whole from the cochlea to the associative cortex; measurements can be taken almost simultaneously, artifacts are practically non-existent, and the constant position and impedance of the pickup electrodes over time keeps down measurement inaccuracy and makes good reproducibility possible. Finally, the relative distance if the pickup electrodes from the cochlear site makes it possible to obtain direct and accurate measurements of all of the far field auditory evoked potentials described above: ABR, AMLR, and ACR. In addition, ABR wave 1 makes it possible by equivalence (cf. Buckard et al., J Acous Soc Am, 93 (4), pp. 2069–2076, April 1993) to measure the same activity as EAP activity and to do so without any need resort to a "subtractive" technique. The device of the invention thus makes it possible to examine and evaluate overall activity of the auditory system in a single operation, including the possibility of recording results. When coupled with a cochlear implant, it also makes it possible to optimize the adjustment thereof, quickly and in "objective" manner, particularly on young children, which is not possible with previously known device.

The invention relies in part on the observation whereby it is possible to measure in reliable manner the electrical potentials that result from neuronal activity of the auditory system by means of at least two electrodes that are remote from the cochlea, i.e. under the skin in the temporo-occipital area; one advantage lies in the device being easier to implant surgically; another advantage lies in the measurement system being less sensitive to artifacts due to the cochlea being stimulated. An essential feature of the measurement method and device of the invention is that because of the external position (relative to the cochlea) of the measurement (i.e. pickup) electrodes, the potential differences that are measured represent physical phenomena that are quite distinct from those represented by measurements using an intracochlear electrode.

Another important advantage of the invention is that it is possible to make use of measurement electrodes that are larger that those which can be implanted in the cochlea; this give rise to contact impedance between the electrodes and tissue which is smaller and which can be kept substantially constant over time; the accuracy and the repeatability of measurements are thus improved; furthermore, the size of the electrode enables it to be associated with a screw passing through the electrodes and enabling it to be secured to bony tissue, thereby improving both the stability over time of its impedance, and also possibility contributing to securing the package of the implant itself.

The measurement technique of the invention is much less sensitive to electrical stimulation artifacts; consequently it is possible to measure and study evoked potentials in the "time window" of about 400 $\mu$s following stimulation, unlike the systems described in the above documents; in addition, the device of the invention is simplified since there is no need for a blanking amplifier, and since there is no longer any point in providing for the electrodes to be short-circuited or open-circuited.

Given that the amplitudes of the detected potential differences are very small, in particular of the order of 0.1 microvolts ($\mu$V) to 10 $\mu$V, i.e. 100 to 1000 times smaller than those measured when a measurement electrode is placed in the cochlea, a third measurement electrode is generally provided which serves as a reference and which is connected to the ground terminal of the differential amplifier: this makes it possible to increase the output signal-to-noise ratio to a considerable extent.

In preferred embodiments:
the pickup electrodes, of which there are at least two, are situated in substantially diametrically opposite positions on either side of the implantable amplifier-transceiver package with is also implanted in the temporo-occipital area; while the electrodes are being surgically implanted, this makes it easy to align them on the portion of the associated auditory system so as to optimize the amplitudes of the signals picked up;
the pickup electrodes can be movable relative to the package so as to be positioned optimally during the operation by the surgeon, e.g. so as to be accurately parallel to the cerebral trunk, and properly spaced apart from each other; to this end, the electrodes are preferably mounted at the end of a support such as a flexible catheter of silicone covering conductive wire linked to the package;
alternatively, the pickup electrodes can be placed on a support in the form of a flexible plate extending around the transceiver package with is also implanted in the temporo-occipital area; after surgical implantation, this make it possible for the practitioner to make use of a multiplexing device incorporated in the implanted package to select two pickup electrodes (from a plurality of implanted electrodes) for forming the best couple for sensing the activity that is to be measured; and
the reference pickup is disposed close to or on the implantable package.

When the implantable device incorporates means for stimulating the auditory nervous system:
the reference stimulation electrode can be mounted to move relative to the package so as to be positioned optimally on the basis of tests performed during the operation, can be then be fixed durably by the surgeon; this optimization can consist in ensuring that the line constituted by stimulation electrodes and the stimulation reference electrodes forms a stimulation dipole that is perpendicular to the line interconnecting the two pickup electrodes, so as to reduce the stimulation artifact;
a plurality of fixed stimulation reference electrodes can be provided connected downstream to a multiplexing device integrated in the package; after surgical implantation, this makes it possible for the practitioner to select the stimulation reference electrodes which best reduce the stimulation artifact; and
provision can also be made for a plurality of pickup electrodes and for a plurality of stimulation reference electrodes to be connected to two respective multiplexing systems thereby enabling adjustments to be optimized after surgery, and thus avoiding the need to perform tests during the operation.

In some cases, the pickup reference electrodes can be the same as the stimulation reference electrode.

The physiological signals as picked up, in particular the auditory evoked potentials, are transferred to the outside via the implanted receiver package by wireless transmission (e.g. at high frequency and by amplitude or frequency modulation).

The device comprising the pickup electrodes, the pickup reference electrode, an the implantable transceiver package can be coupled to or integrated with a device for acoustic, and/or electrical, and/or mechanical stimulation that can be extracochlear and/or intracochlear. In which case, it constitutes a stimulation implant fitted with a telemetry device serving to evaluate or monitor its action. By way of example, the device of the invention can:
either be a cochlear implant for severe or profound deafness, having one or more intracochlear stimulation electrodes fitted with a device for picking up auditory evoked potentials enabling optimum adjustments to be made of detection thresholds, of discomfort thresholds, and the acoustic-electrical compression function;
or an auditory for severe or profound deafness including one or more extracochlear stimulation electrodes; such an implant preferably includes an electrical stimulation electrode suitable for fixing to the stapes; it is naturally fitted with the same device for picking up auditory evoked potentials enabling optimum adjustments to be performed;

or an auditory implant for medium or severe deafness including a device for stimulating the auditory system mechanically such as a vibrator, which device is preferably suitable for positioning on the oval window of the cochlea, or in the temporo-occipital area;

or else an implant for canceling tinnitus, fitted with a device for picking up auditory evoked potential so as to achieve optimum adjustment of the electrical stimulation.

BRIEF DESCRIPTION OF THE DRAWINGS

Other advantages and characteristics of the invention will be understood from the following description which refers to the accompanying drawings, showing preferred embodiments of the invention without limiting the invention thereto in any way.

FIG. 1A shows an implantable device constituting a first embodiment.

FIG. 1B shows an implantable device constituting a second embodiment.

FIG. 2A is a diagram showing the transcutaneous transmission system between an implanted device and an external device for analyzing signals.

FIG. 2B shows the electrodes connected to an amplifier whose output is connected to a transmitter and to a signal processing module.

FIG. 2C shows a variant of FIG. 2B in which a plurality of pickup electrodes such as those shown in FIG. 1B are connected to the amplifier by two multiplexers.

DETAILED DESCRIPTION OF THE PREFERRED EMBODIMENTS

Figure 3:
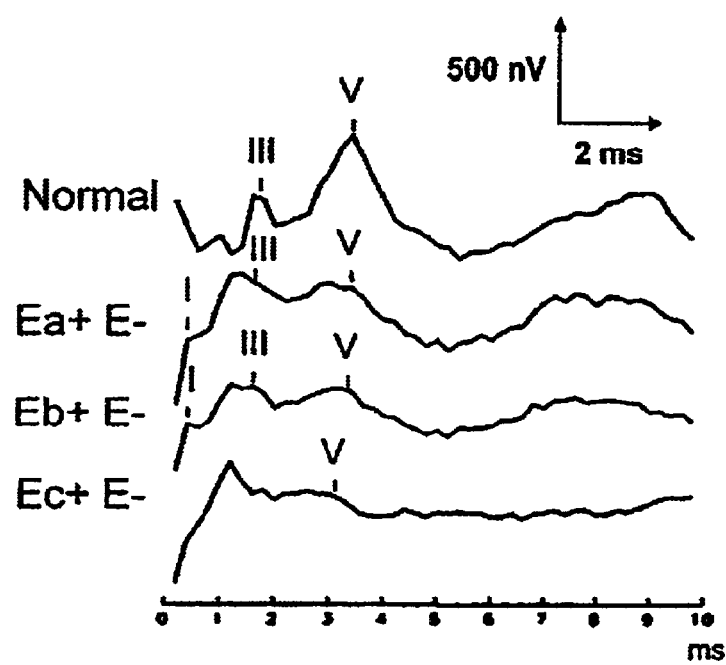
FIG. 3 shows four waveforms of voltages measured in four respective configurations for pickup electrode implantation.

FIG. 1A shows an implantable device that makes it possible firstly to pick up biological electrical signals characteristic of auditory evoked potentials, and to do so via positive and negative pickup electrodes (E+ and E−) connected via representative wireless 1 and 3 to an amplifier module 4 contained in a sealed package 2, and secondly to transmit these signals, or signals derived therefrom, to the outside of the body via a transmitter module 5 contained in the package 2, with this being done at radio frequency. A coil or antenna 31 of the transmitter module 5 can equally well be inside or outside the package 2. The package contains an optional signal processor module 6. In this case, the reference electrode (RR) is fixed to the package and is used to make it possible to perform differential amplification between the two pickup electrodes. The power required to operate the implant can either come from an implant cell or battery, or else it can be transmitted via an external coil using electromagnetic induction.

The device shown in FIG. 1B has a grid of thirty-two electrodes 7a that are regularly spaced apart on a flexible plate 30 and that are connected by respective wires 7b (drawn as dashed lines) to a multiplexer module 8 contained inside the package 2, and it makes it possible by electronic switching to select those two electrodes which are found to form an optimum couple for picking up the physiological activity which is to be measured, such couples differing in the orientation and in the spacing of their electrodes relative to each other; the distance between the electrodes preferably lies in the range 40 mm to 80 mm (with a distance of about 60 mm generally being found to be optimal).

FIG. 2A shows the principle on which the device operates. The implantable device 9 as shows in FIG. 1 is used to pick up the electrical physiological activity that follows stimulation of the auditory system, and to transmit it through the skin 10 of the patient to an external unit 11 for analyzing said activity.

Transmission is performed transcutaneously and makes metallic isolation possible. FIG. 2B is a general block diagram showing how said device with two pickup electrodes E+ and E− operates; FIG. 2C is a block diagram showing a device having a number $n_1$ of pairs of pickup electrodes $E_i$ connected to the inputs of the amplifier 4.

FIG. 3 shows three examples of reading (of voltage as a function of time) obtained using the device implanted with the pickup electrodes in the temporo-occipital area. The curves show that the distance between the two pickup electrodes has a considerable influence on the way in which the characteristics of precocious auditory evoked potentials (ABR) are picked up. Unlike standard extracorporeal pickup (top curve referenced herein as "normal") as made by means of a positive surface electrode on the forehead and by means of a negative surface electrode on the homolateral mastoid, the quality of the ABR pickup varies depending on the distance between the two implanted pickup electrodes: the results obtained with two electrodes Ea+ and E− spaced apart by 60 mm are of significantly better than those obtained with two electrodes Eb+ and E− spaced apart by 45 mm, which are clearly better than those obtained with two electrodes Ec+ and E− spaced apart by 30 mm. The device of the invention preferably has pickup electrodes that are spaced apart by more than 30 mm.

Figure 4:
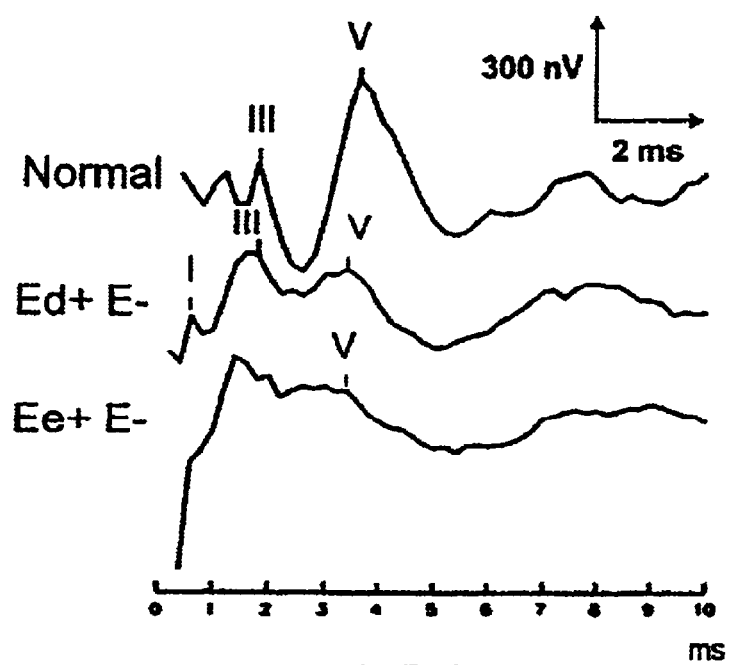
FIG. 4 shows three waveforms of voltages measured in three respective configurations of pickup electrode implantation.

FIG. 4 gives other reading that show that the orientation of the pickup electrodes relative to the activity that is to be measured, in this case the cerebral trunk, has an influence on the picking up of positive evoked potentials. Unlike a standard extracochlear pickup (referenced "normal" in this case; a positive surface electrode on the forehead, and a negative surface electrode on the homolateral mastoid), the quality of the PEAP signals picked up decreases as a function of the orientation of the two pickup electrodes implanted in the temporo-occipital area, relative to the activity to be measured: the results obtained with the cerebral trunk are better than those obtained with two electrodes Ee+ and E− oriented at 28° to the cerebral trunk. The device of the invention which is adapted to obtain PEAP measurements must be oriented so that the pickup electrodes are as parallel as possible to the cerebral trunk.

Figure 5:
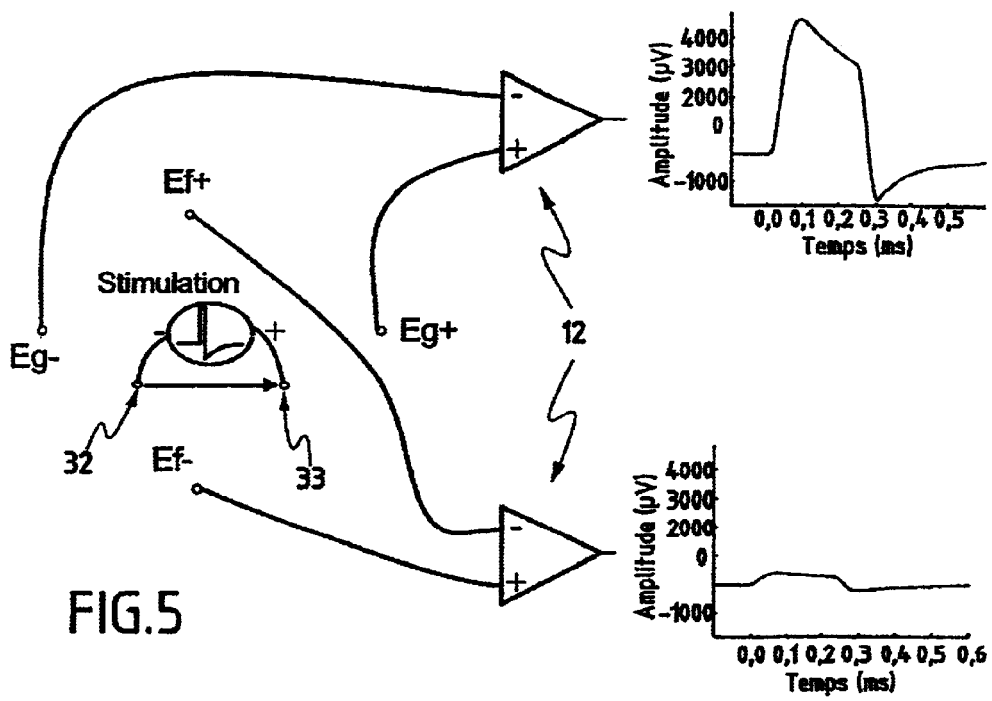
FIG. 5 shows two variant implantations for stimulation electrodes, and two artifact waveforms corresponding respectively to these two implantations.

FIG. 5 shows that during electrical stimulation of the auditory system, the orientation of the pickup electrodes relative to the stimulation electrodes 32 and 33 influences how the stimulation artifact is picked up. With a pickup position that is parallel to the stimulation (Eg+Eg−), the amplitude of the stimulation artifact output the differential amplifier 12 is at a maximum. With a pickup position that is perpendicular to the stimulation (Ef+Ef−) the amplitude of the stimulation artifact output the differential amplifier 12 is at a maximum. The device of the invention preferably includes pickup electrodes perpendicular to the equivalent stimulation dipole.

Figure 6:
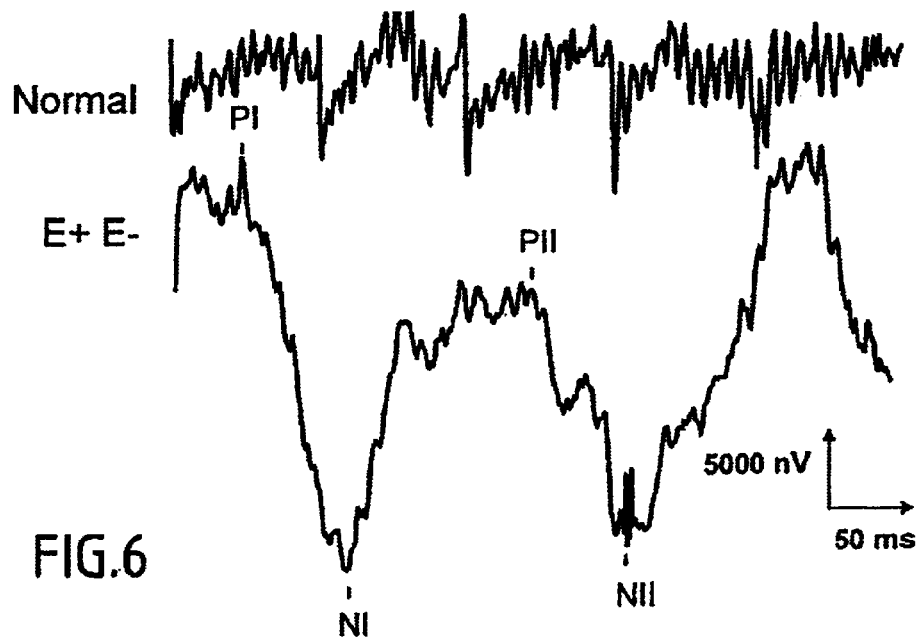
FIG. 6 is a waveform of measurement by surface electrodes, and a waveform that results from averaging measurements performed by the device if FIG. 1A.

FIG. 6 shows how late auditory evoked potentials (ALCR) following electrical intracochlear stimulation are picked up, firstly using conventional surface electrodes (referenced "normal" in the drawing) and secondly using the device shown in FIG. 1A (referenced E+E−).

The distance between the + and the − electrodes of the differential amplifier is about 60 mm and seems to be a good compromise for maximum attenuation of artifact and easy surgical implantation. It has been found that an average of 100 readings can suffice to obtain such an ACLR of good quality. This can be explained by the fact that the amplitude of the NI, PI, NII, and PII waves is of the order of 25 $\mu$V, i.e. ten times that obtained using a pickup device having external surface electrodes ("Les potentiels évoqués auditifs" [Auditory evoked potentials] by J. M. Guerit, 1993, published by Masson, Paris, at pages 87 to 99 on evoked potentials).

Figure 7A:
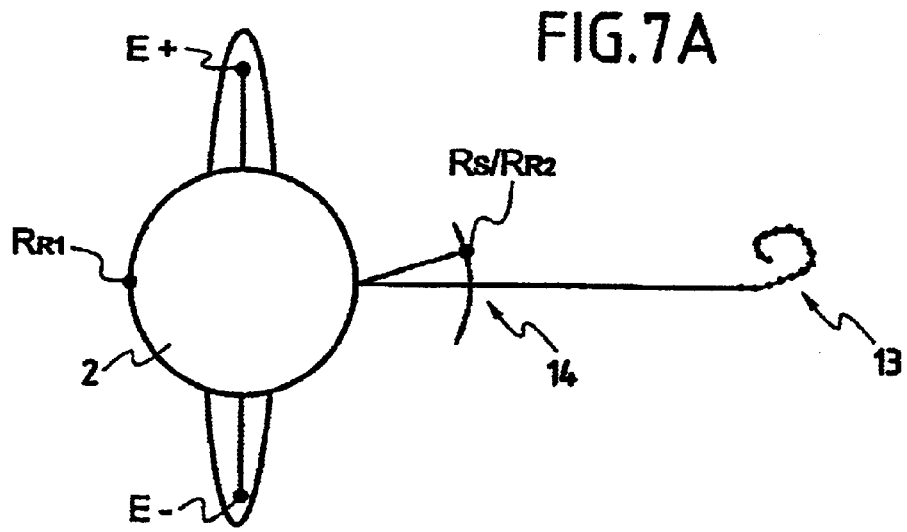
FIG. 7A shows an implantable device constituting a third embodiment.
Figure 7B:
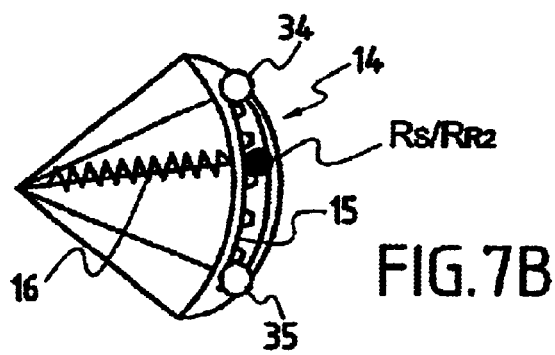
FIG. 7B shows the device for orienting the electrodes of FIG. 7A.

FIG. 7A shows a cochlear implant designed to be implanted in the temporo-occipital area and fitted with a telemetry device for measuring auditory evoked potentials and for transmitting the measurements by radio. This implant makes it possible simultaneously to stimulate the cochlea via the intracochlear electrode 13 (which may comprise single electrode or a plurality of distinct electrodes) and stimulation reference electrodes RS, and to pick up the activity of the auditory system via the electrodes E+ and E−. When using differential amplification, the reference electrode can either be fixed (RR1) or moving (RR2). In particular embodiment the stimulation reference electrode RS can be used as the pickup reference electrode RR2. All of the electronics required for stimulation, pickup, and transmission, purposes is situated in the sealed package 2. The antenna(s) or coil(s) for communications, and where appropriate for power transmission, can be located equally well inside the package 2 or outside it. A device 14 serves to orient the stimulation dipole by displacing the electrode RS/RR2. FIG. 7B shows an embodiment of the device 14 comprising an electrode RS/RR2 which is guided by a sliding system having a plurality of notched positions 15. A flexible silicone-insulated and spiral-wound electric wire 16 makes it possible to move the electrode RS/RR between two extreme positions an d without giving rise to significant mechanical stress.

Figure 8:
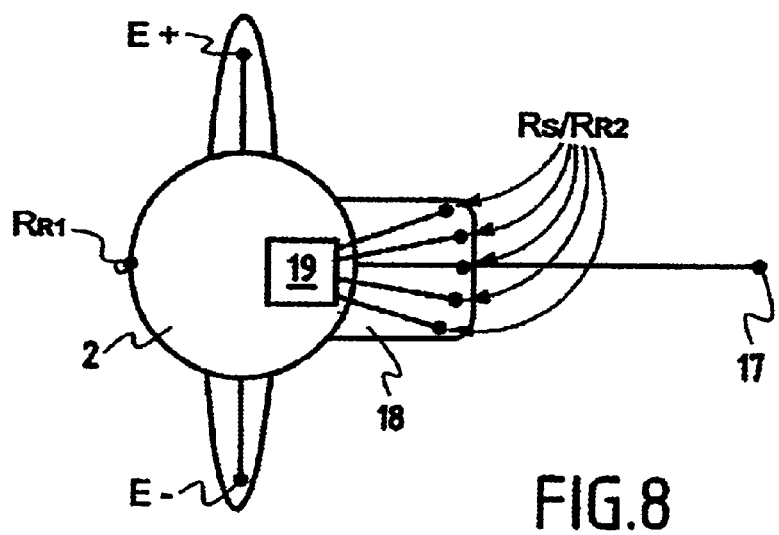
FIG. 8 shows an implantable device constituting a fourth embodiment.

FIG. 8 shows an extracochlear stimulation device provided with one or more stimulation electrodes 17 and including a telemetry device for measuring evoked potentials. By providing electrical stimulation via the electrode 17 (comprising one or more distinct electrodes)and the stimulation reference electrode RS, it enables the electrical activity of the auditory system to be picked up via the electrodes E+ and E−. In particular embodiment the stimulation reference electrode RS can be used as the pickup reference electrode (in this case RR2). The device is also fitted with plurality of pickup reference electrodes RS/RR2 placed on a support 18 and connected by wires to a switch module 19 situated the sealed package 2, thereby enabling a particular electrode RS/RR2 to be selected. The "pickup" reference electrode (RR1 or RS/RR2) can be used to make differential amplification between the two pickup electrodes possible. All of the electronics required for stimulation, pickup, and transmission purposes is situated in the package 2. The antenna(s) or coil(s) for communications, and where appropriate for power transmission, can be located equally well inside the package 2 or outside it.

Figure 9A:
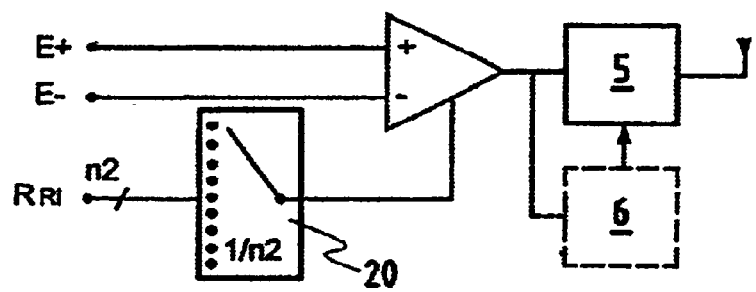
FIG. 9A shows how a plurality of stimulation electrodes RRi are connected to the stimulation module via two demultiplexers.
Figure 9B:
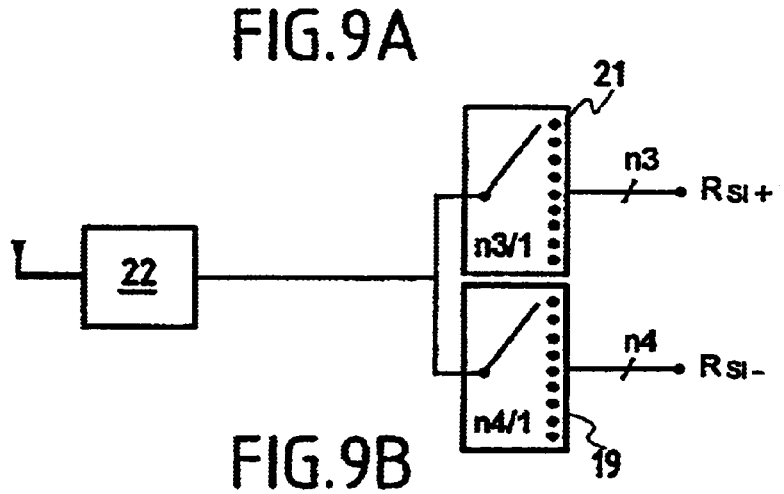

The implants shown in FIGS. 7 and 8 can be fitted either with a single fixed or moving electrode RR1, or with a plurality of electrodes RR1 (and/or RR2) managed by switch 19, or with a single electrode RS/RR2 which is fixed or which preferably moving, or else with a plurality of electrodes RS/RR2 managed by a switch 19. The power required for the implant to operate can either come from an implantable battery or else it can be transmitted by electromagnetic induction via an external coil:

FIGS. 9A and 9B are diagrams showing how an implant of the type shown in FIGS. 7 and 8 operates.

FIG. 9A corresponds to the "pickup" portion of the device. The module 20 is a multiplexing circuit which makes it possible to select the reference electrode from the $n_2$ available electrodes RRi.

FIG. 9B corresponds to the electrical "stimulation" portion of the device. The module 21 is a demultiplexer circuit which selects the positive electrode of the stimulator from the $n_3$ available electrodes Rsi+.

The module 19 is a demultiplexer circuit which selects the negative electrode of the stimulator from the $n_4$ available electrodes Rsi−.

The module 22 controls the two multiplexers 19 and 21 as a function of the information it receives from the outside via an antenna.

Figure 10A:
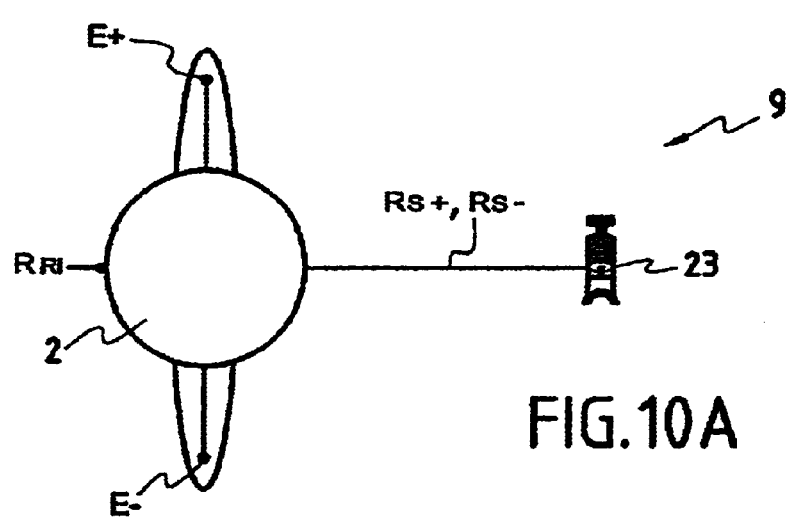
FIG. 10A shows an implantable device constituting a fifth embodiment.
Figure 10B:
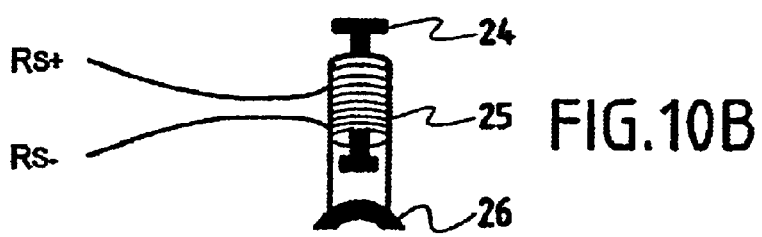
FIG. 10B shows the electromechanical transducer of FIG. 10A on a larger scale

FIG. 10A shows a mechanical stimulator for the middle ear fitted with a telemetry device for measuring auditory evoked potentials. By stimulating the oval window of the cochlea by mechanical vibration, this implant makes it possible to pick up the activity of the auditory system via the electrodes E+ and E−. The vibrator 23 used for mechanical stimulation is shown in FIG. 10B. After surgery very similar to that performed for the pathology known as otospongiosis, the vibrator replaces the ear bone known as the stapes. The end 24 rests against the oval window instead of the plate of the stapes. The transducer 25 which transforms an electrical signal into mechanical energy can be magnetic or piezoelectric. Its function is to move the portion 24 relative to the portion 26 as a function a control signal coming from the package 2 and conveyed by the two wires RS+ and RS−. All of the electronics required for stimulation, pickup, and transmission purposes is situated in the sealed package 2. The antenna(s) or coil(s) for communications, and where appropriate for power transmission, can be located equally sell inside the package 2 or outside it.

What is claimed is:

1. A method for measuring auditory evoked potentials of an auditory system of a patient or animal body, said comprising:

surgically implanting at least two pickup electrodes in the temporo-occipital area inside said body, picking up electrical signals resulting from neuronal activity of said auditory system by means of said at least two pickup electrodes, and producing signals representative of neuronal activity of said auditory system from said electrical signals sensed by said pickup electrodes.

2. The method according to claim 1 wherein said at least two extracochlear pickup electrodes are surgically implanted in the temporo-occipital area of said body, so that a line linking said pickup electrodes is substantially parallel to the cerebral trunk of said body.

3. The method according to claim 1 wherein said electrical signals have an amplitude between 0.1 $\mu V$ and 10 $\mu V$.

4. The method according to claim 1 further comprising stimulating said auditory system by stimulation means implanted in said auditory system, thereby generating said neuronal activity of said auditory system.

5. The method according to claim 4 wherein said stimulation means are implanted in the cochlea of said auditory system.

6. The method according to claim 4 wherein said stimulation means are implanted outside of the cochlea of said auditory system.

7. The method according to claim 1 further comprising acoustically stimulating said auditory system by stimulation means implanted in said auditory system, thereby generating said neuronal activity of said auditory system.

8. The method according to claim 1 further comprising mechanically stimulating said auditory system by a vibrator implanted in said auditory system, thereby generating said neuronal activity of said auditory system.

9. The method according to claim 1 further comprising electrically stimulating said auditory system by at least one stimulation electrode implanted in said auditory system, thereby generating said neuronal activity of said auditory system.

10. The method according to claim 9 wherein said at least one stimulation electrode forms a stimulation dipole which is surgically implanted so as to be substantially perpendicular to a line linking said at least two pickup electrodes.

11. The method as in claim 10 further comprising positioning said stimulation dipole with respect to said at least two pickup electrodes so as to reduce stimulation artifact in said electrical signals resulting from neuronal activity of said auditory system.

12. The method according to claim 1 further comprising:

surgically implanting a plurality of electrodes in the temporo-occipital area in said body, and selecting said at least two pickup electrodes and at least one stimulation electrode from said plurality of electrodes, based on quality of signals detected by said pickup electrodes.

13. The method according to claim 12 further comprising selecting a pickup reference electrode and a stimulation reference electrode from said plurality of electrodes.

14. The method according to claim 1 further comprising stimulating at least a portion of said auditory system by means of at least one surgically implanted vibrator.

15. The method as in claim 1 further comprising amplifying said electrical signals resulting from neuronal activity of said auditory system, and transmitting the amplified electrical signals through the skin of said body, and producing said signals representative of neuronal activity of said auditory system from said transmitted electrical signals.

* * * * *